US012783381B2

(12) United States Patent
Matsuno et al.

(10) Patent No.: US 12,783,381 B2
(45) Date of Patent: Nov. 3, 2026

(54) INFORMATION PROCESSING DEVICE, INFORMATION PROCESSING METHOD, AND RECORDING MEDIUM

(71) Applicant: NEC Corporation, Tokyo (JP)

(72) Inventors: Ryuta Matsuno, Tokyo (JP); Keita Sakuma, Tokyo (JP)

(73) Assignee: NEC CORPORATION, Tokyo (JP)

( * ) Notice: Subject to any disclaimer, the term of this patent is extended or adjusted under 35 U.S.C. 154(b) by 351 days.

(21) Appl. No.: 18/559,113

(22) PCT Filed: Mar. 6, 2023

(86) PCT No.: PCT/JP2023/008239

§ 371 (c)(1),
(2) Date: Nov. 6, 2023

(87) PCT Pub. No.: WO2024/184986

PCT Pub. Date: Sep. 12, 2024

(65) Prior Publication Data

US 2025/0094308 A1 Mar. 20, 2025

(51) Int. Cl.
*G06F 11/34* (2006.01)
*G16H 50/20* (2018.01)

(52) U.S. Cl.
CPC ......... *G06F 11/3447* (2013.01); *G16H 50/20* (2018.01)

(58) Field of Classification Search
CPC ............................ G16H 50/20; G06F 11/3447
See application file for complete search history.

(56) References Cited

U.S. PATENT DOCUMENTS 5,918,200 A * 6/1999 Tsutsui .................... G05B 13/04 706/54
11,257,592 B2 * 2/2022 Perera .................... G16H 10/60
11,526,953 B2 * 12/2022 Bonageri ............... G16H 50/20
11,610,679 B1 * 3/2023 Zhan ...................... G06N 3/096
(Continued)

FOREIGN PATENT DOCUMENTS

CN 115223087 A 10/2022
JP 2021039491 A * 3/2021
(Continued)

OTHER PUBLICATIONS

English translation of Written opinion for PCT Application No. PCT/JP2023/008239.
(Continued)

*Primary Examiner* — Thomas D Alunkal

(57) ABSTRACT

In order to provide a model evaluation method in which a plurality of groups are considered, an information processing device according to the present invention includes a data acquisition means that acquires at least one condition for evaluation data of a machine learning model, a performance calculation means that calculates a performance index of the machine learning model and a performance index of the machine learning model after being updated using a data set specified for each of the at least one condition, and an index calculation means that calculates a deterioration index of a performance of the machine learning model based on the performance indexes before and after the machine learning model is updated.

11 Claims, 9 Drawing Sheets

(56) References Cited

U.S. PATENT DOCUMENTS

| | | | | |
|---|---|---|---|---|
| 12,013,824 | B1 * | 6/2024 | Reeves | G06F 11/3006 |
| 12,597,488 | B2 * | 4/2026 | Schobel | G06N 20/20 |
| 2015/0379432 | A1 * | 12/2015 | Ando | G16H 50/20<br>706/14 |
| 2016/0371601 | A1 * | 12/2016 | Grove | G06N 20/00 |
| 2019/0132191 | A1 * | 5/2019 | Mann | G06F 11/008 |
| 2020/0349466 | A1 * | 11/2020 | Hoogerwerf | G06N 5/045 |

FOREIGN PATENT DOCUMENTS

| | | | |
|---|---|---|---|
| JP | 2021-117926 | A | 8/2021 |
| JP | 2021-131757 | A | 9/2021 |
| WO | 2014/155690 | A1 | 10/2014 |
| WO | 2022/185444 | A1 | 9/2022 |
| WO | 2022/254944 | A1 | 12/2022 |

OTHER PUBLICATIONS

Japanese Office Action for JP Application No. 2025-504922, mailed on Jun. 2, 2026 with English Translation.

Martin Bertran et al., "Distributionally Robust Group Backwards Compatibility," arXiv:2112.10290v1 [online], Dec 20, 2021, [Retrieved on May 25, 2025], Retrieved from The Internet URL<https://arxiv.org/pdf/2112.10290v1>.

* cited by examiner

Fig. 4

| DATA No. | GROUP | PRE-UPDATE MODEL | POST-UPDATE MODEL | | |
|---|---|---|---|---|---|
| | | | MACHINE LEARNING MODEL 1 | MACHINE LEARNING MODEL 2 | MACHINE LEARNING MODEL 3 |
| 1 | 0 | ○ | | ○ | ○ |
| 2 | 0 | ○ | | | |
| 3 | 0 | | | | ○ |
| 4 | 0 | | ○ | | ○ |
| 5 | 1 | ○ | ○ | ○ | |
| 6 | 1 | ○ | ○ | ○ | ○ |
| 7 | 1 | ○ | | ○ | ○ |
| 8 | 1 | | ○ | ○ | ○ |
| 9 | 1 | | ○ | ○ | |
| 10 | 1 | | ○ | | |
| ACCURACY FOR ALL DATA | | 50% | 60% | 60% | 60% |
| ACCURACY FOR GROUP 0 | | 50% | 25% | 25% | 75% |
| ACCURACY FOR GROUP 1 | | 50% | 83% | 83% | 50% |
| BTC | | | 40% | 80% | 60% |
| DEGRADATION INDEX | | | 25% | 25% | 0% |

○: EVALUATION DATA OF WHICH LABEL MATCHES PREDICTION RESULT OF EACH MACHINE LEARNING MODEL

INFORMATION PROCESSING DEVICE, INFORMATION PROCESSING METHOD, AND RECORDING MEDIUM

This application is a National Stage Entry of PCT/JP2023/008239 filed on Mar. 6, 2023, the contents of all of which are incorporated herein by reference, in their entirety.

TECHNICAL FIELD

The present invention relates to an evaluation of a machine learning model.

BACKGROUND ART

PTL 1 discloses a method of evaluating compatibility between a pre-update model and a post-update model when a machine learning model is updated.

CITATION LIST

Patent Literature

PTL 1: WO 2022/185444 A

SUMMARY OF INVENTION

Technical Problem

According to the technique described in PTL 1, compatibility in overall performance is evaluated. However, it may be desirable that the performance evaluation of the machine learning model is performed for each of a plurality of groups such as a plurality of departments in a company or the like or a plurality of viewpoints with respect to an evaluation target.

An object of the present invention is to provide an evaluation of a machine learning model in which a plurality of groups are considered.

Solution to Problem

An information processing device according to an aspect of the present invention includes a data acquisition means that acquires at least one condition for evaluation data of a machine learning model, a performance calculation means that calculates a performance index of the machine learning model and a performance index of the machine learning model after being updated using a data set specified for each of the at least one condition, and an index calculation means that calculates a deterioration index of a performance of the machine learning model based on the performance indexes before and after the machine learning model is updated.

An information processing device according to an aspect of the present invention includes a data acquisition means that acquires at least one condition for evaluation data of a machine learning model, a performance calculation means that calculates a performance index of the machine learning model using a data set specified for each of the at least one condition, and a learning means that causes the machine learning model to perform relearning based on the performance index.

An information processing method according to an aspect of the present invention includes acquiring at least one condition for evaluation data of a machine learning model, calculating a performance index of the machine learning model and a performance index of the machine learning model after being updated using a data set specified for each of the at least one condition, and calculating a deterioration index of a performance of the machine learning model based on the performance indexes before and after the machine learning model is updated.

A recording medium according to an aspect of the present invention records a program for causing a computer to execute acquiring at least one condition for evaluation data of a machine learning model, calculating a performance index of the machine learning model and a performance index of the machine learning model after being updated using a data set specified for each of the at least one condition, and calculating a deterioration index of a performance of the machine learning model based on the performance indexes before and after the machine learning model is updated.

Advantageous Effects of Invention

According to the present invention, a machine learning model can be evaluated in consideration of a plurality of groups.

BRIEF DESCRIPTION OF DRAWINGS

FIG. 4 is a diagram for explaining a degradation index of the information processing device.

EXAMPLE EMBODIMENT

Figure 1:
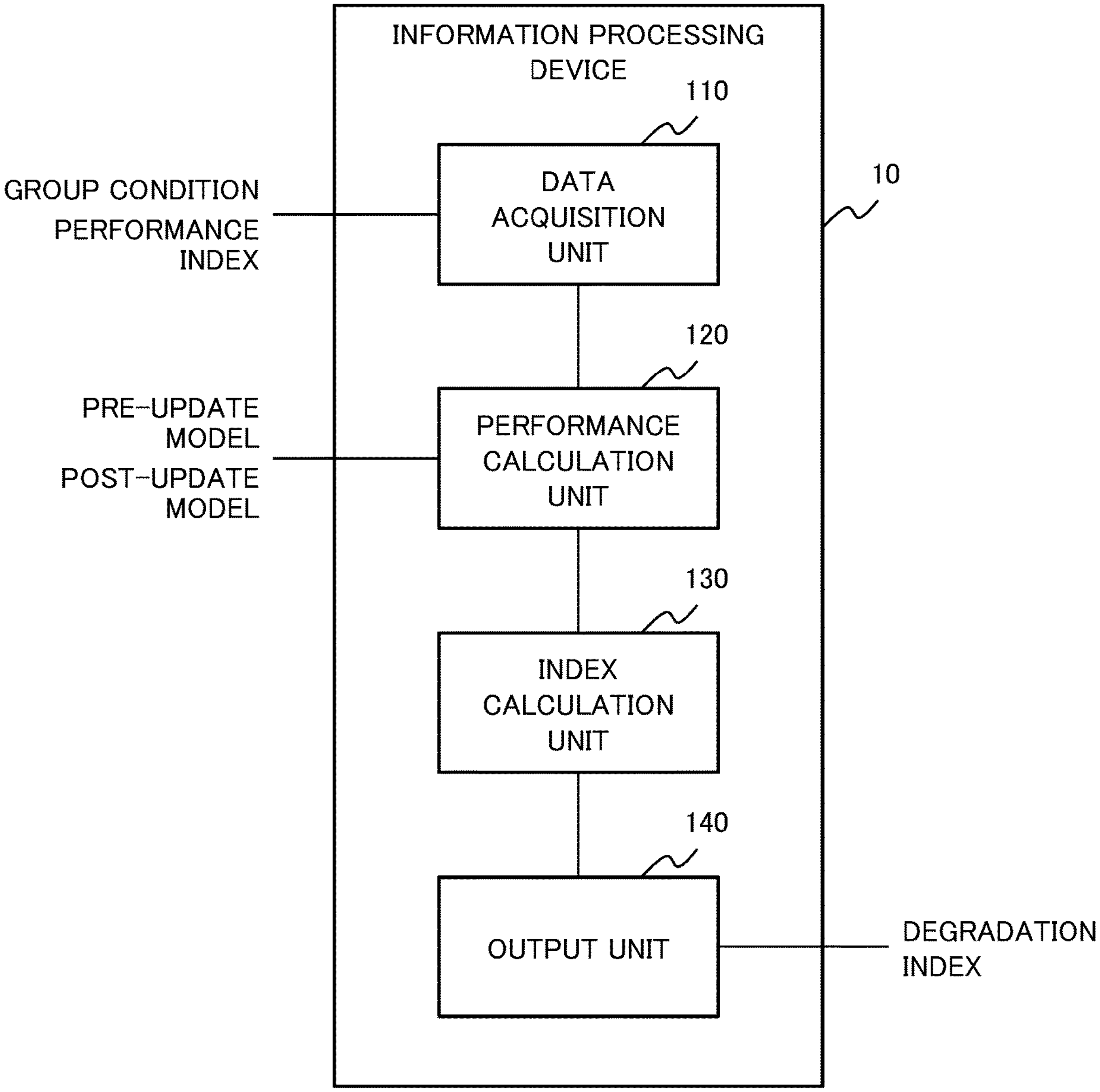
FIG. 1 is a block diagram illustrating an example of a configuration of an information processing device according to a first example embodiment.

Hereinafter, example embodiments of the present invention will be described with reference to the drawings. However, the example embodiments are not limited to the description of the drawings.

First Example Embodiment (Concerning Machine Learning Model)

A machine learning model that is a premise in the present example embodiment will be described. The machine learning model is information indicating a relationship between an explanatory variable and an objective variable. The machine learning model is, for example, a component for estimating a result of an estimation target by calculating an objective variable based on an explanatory variable.

The machine learning model is generated by executing a learning algorithm using learning data in which the value of the objective variable has already been obtained and a certain parameter as inputs. The machine learning model may output a variable that describes a probability distribution of an objective variable. The machine learning model may be described as a "learning model", an "analysis model", an "AI model", a "trained model", an "inference model", a "prediction formula", or the like.

The explanatory variable is a variable used as an input in the machine learning model. The explanatory variable may be described as a "feature amount", a "feature", or the like.

The learning algorithm for generating the machine learning model is not particularly limited, and may be an existing learning algorithm. For example, the learning algorithm may be a random forest, a support vector machine, Naive Bayes, a neural network, or a piecewise linear model using factorized asymptotic bayesian (FAB) inference, or a neural network.

A method of a piecewise linear model using FAB inference is disclosed in, for example, US 2014/0222741 A1.

(Concerning Update of Machine Learning Model)

The performance of the machine learning model as described above may deteriorate due to a change in environment. When the accuracy of the machine learning model decreases, a user of the machine learning model re-train the machine learning model (also referred to as a "pre-update model") to improve the accuracy of the updated machine learning model (also referred to as a "post-update model").

However, users may evaluate the performance of the machine learning model from various perspectives. For example, a machine learning model that predicts purchases of products in a store will be described as an example. A store manager who operates the store evaluates the performance of the machine learning model using the accuracy of all purchases in the store. However, a person in charge on weekdays evaluates the performance of the machine learning model using the accuracy of purchases on weekdays rather than the accuracy of all purchases. On the other hand, a person in charge on weekends evaluates the performance of the machine learning model using the accuracy of purchases on weekends.

In this way, the users evaluate the performance of the machine learning model from various perspectives. Therefore, it is preferable to divide data for evaluating performance of machine learning into several groups of units to evaluate the performance of the machine learning model.

At this point, an information processing device 10 according to a first example embodiment outputs an index for evaluating the post-update model in consideration of the plurality of groups.

In the following description, the pre-update model, the post-update model, and the evaluation data are stored at any location, and a device for storing them is not limited. For example, the information processing device 10 may operate after a pre-update model and a post-update model are acquired and stored, or may operate using a pre-update model and a post-update model stored in a device that is not illustrated. Alternatively, the information processing device 10 may operate after a data set related to a group is stored in advance, or may operate while acquiring data.

(Configuration of Device)

FIG. 1 is a block diagram illustrating an example of a configuration of the information processing device 10 according to the first example embodiment. The information processing device 10 includes a data acquisition unit 110, a performance calculation unit 120, an index calculation unit 130, and an output unit 140.

The data acquisition unit 110 acquires a group condition for specifying a group in which each piece of data (also referred to as "evaluation data" or "data to be evaluated") used for prediction by the model is included. The group condition is a condition for specifying a group (also referred to as a "data set") in which each piece of evaluation data is included.

The evaluation data is data including an explanatory variable (x) and an objective variable (y). At least some of the evaluation data may belong to a plurality of groups. For example, the above-described machine learning model that predicts purchases of products in a store will be described as an example. The evaluation data of the machine learning model used in a certain store is a data set including all data measured in the store as elements. The group "weekday" is a data set of data measured at the store, under the condition that the data are measured on weekdays. The group "midnight time zone" is a data set of data measured at the store, under the condition that the data are measured in the midnight time zone. In this case, data measured in midnight time zones on weekdays belongs to the group "weekday" and the group "midnight time zone".

The data acquisition unit 110 may acquire a performance index for evaluating the performance of the machine learning model. When the data acquisition unit 110 acquires the performance index, the performance calculation unit 120 to be described later calculates the acquired performance index. The data acquisition unit 110 may acquire a calculation method such as a performance calculation formula.

The performance index is an index for evaluating the performance of the machine learning model. An example of the performance index in the present example embodiment is an index of which a value is higher as the performance is higher. For example, in the case of a discrimination model, the performance index is accuracy, correct answer rate, matching rate, reproduction rate, F measure (F1 score), FB score, receiver operating characteristic curve (ROC)-area under the curve (AUC), or precision recall curve (PR)-AUC. However, the performance index is not limited thereto. For example, in the case of a regression model, the performance index may be a coefficient of determination.

The performance calculation unit 120 calculates a performance index of the pre-update model and a performance index of the post-update model using the group defined according to the group condition acquired by the data acquisition unit 110. Hereinafter, the performance index of the pre-update model will be referred to as a "pre-update performance", and the performance index of the post-update model will be referred to as a "post-update performance".

In at least some of the groups, the performance calculation unit 120 may calculate a post-update performance by using some of the evaluation data included in the group, rather than using all the evaluation data included in the group. When some of the data is used, data used for calculating a pre-update performance may be different from data used for calculating a post-update performance in at least some of the groups.

(Detailed Method of Calculating Degradation Index)

The index calculation unit 130 calculates a degradation index (also referred to as "deterioration index") indicating a deterioration of the performance of the post-update model relative to the pre-update model based on the pre-update performance and the post-update performance for each of the groups. A low value of the degradation index indicates that the post-update model is a good model. For example, the index calculation unit 130 calculates the degradation index based on a difference between the pre-update performance and the post-update performance. More specifically, the index calculation unit 130 may calculate an index represented by the following Formula 1 as a degradation index.

[Formula 1]

$$\text{Index} = \frac{1}{Z_g}\sum_{s\in S}\max\left(0, \frac{M_s(h_1, \{(x, y) \in \mathcal{D}_1 \mid s(h_1, x, y) = 1\}) - M_s(h_2, \{(x, y) \in \mathcal{D}_2 \mid s(h_2, x, y) = 1\})}{Z_s}\right) \tag{1}$$

The index of Formula 1 is a value obtained by summing up deteriorations in performance of the post-update model relative to the pre-update model for the plurality of groups and normalizing the sum using a normalization coefficient. In Formula 1, the second term of max(x,y) indicates a deterioration in performance. The function max(x,y) is a function that returns the larger-value argument of the two arguments (x,y). The coefficient $Z_g$ in Formula 1 is a normalization coefficient that entirely normalizes the sum of the terms of the max function.

The second term of the max function in Formula 1 takes a positive value when the performance index of the post-update model deteriorates as compared with the pre-update performance. On the other hand, when the post-update performance improves as compared with the pre-update performance, the second term of the max function takes a negative value. Therefore, the max function becomes a positive value when the performance of the post-update model deteriorates as compared with the performance of the pre-update model, and becomes 0 when the performance of the post-update model improves as compared with the performance of the pre-update model.

The second term of the function max(x,y) in Formula 1 will be described in detail. The coefficient $Z_s$ included in the second term of the function max(x,y) of Formula 1 is a normalization coefficient for a deteriorating amount of the performance of the post-update model as compared with the pre-update model in the group. The function $M_s(h_n, \{(x,y)\})$ is a function that outputs a performance index of a model $h_n$ for the set {(x,y)}. $h_1$ refers to a pre-update model. $h_2$ refers to a post-update model. $D_1$ is a data set used to calculate a pre-update performance. $D_2$ is a data set used to calculate a post-update performance. $D_1$ and $D_2$ may be the same data set or different data sets.

The function $M_s(h_n, \{(x,y)\})$ in Formula 1 will be described in detail. The function s(f,x,y) in the function $M_s(h_n, \{(x,y)\})$ of Formula 1 is an element included in the set S, and is a function that outputs 1 (True) when the set of f, x, and y satisfies the condition and outputs 0 (False) when the set of f, x, and y does not satisfy the condition.

The index calculation unit 130 may use an index represented by Formula 2. Formula 2 is a formula for calculating a degradation index for each of the plurality of groups based on the difference between the pre-update performance and the post-update performance, and selecting the largest one of the calculated degradation indexes.

[Formula 2]

$$\text{Index} = \max_{s\in S}\max\left(0, \frac{M_s(h_1, \{(x, y) \in \mathcal{D}_1 \mid s(h_1, x, y) = 1\}) - M_s(h_2, \{(x, y) \in \mathcal{D}_2 \mid s(h_2, x, y) = 1\})}{Z_s}\right) \tag{2}$$

When the index calculation unit 130 uses a performance index of which a value is smaller as the performance is better, the index calculation unit 130 may use Formulas 3 and 4 in which the sign of the second term of the function max(x,y) in Formulas 1 and 2 is inverted.

[Formula 3]

$$\text{Index} = \frac{1}{Z_g}\sum_{s\in S}\max\left(0, \frac{M_s(h_2, \{(x, y) \in \mathcal{D}_2 \mid s(h_2, x, y) = 1\}) - M_s(h_1, \{(x, y) \in \mathcal{D}_1 \mid s(h_1, x, y) = 1\})}{Z_s}\right) \tag{3}$$

[Formula 4]

$$\text{Index} = \max_{s\in S}\max\left(0, \frac{M_s(h_2, \{(x, y) \in \mathcal{D}_2 \mid s(h_2, x, y) = 1\}) - M_s(h_1, \{(x, y) \in \mathcal{D}_1 \mid s(h_1, x, y) = 1\})}{Z_s}\right) \tag{4}$$

As examples of the above-described normalization coefficients $Z_s$ and $Z_g$, the index calculation unit 130 may use, but not limited to, the following averages (A) to (C).

(A) Macro average: In a case where an average value of pre-update performances for each group is used as an index, a normalization coefficient is as follows.

[Formula 5]

$$Z_s = M_s(h_1, \{(x, y) \in \mathcal{D}_1 \mid s(h_1, x, y) = 1\}),\ Z_g = |S| \tag{5}$$

(B) Weighted average

In a case where an average value weighted based on the pre-update performances is used as a degradation index, a normalization coefficient is as follows.

[Formula 6]

$$Z_s = 1,\ Z_g = \sum_s M_s(h_1, \{(x, y) \in \mathcal{D}_1 \mid s(h_1, x, y) = 1\}) \tag{6}$$

In a case where an average value weighted based on the number of pieces of data belonging to the group is used as a degradation index, a normalization coefficient is as follows.

[Formula 7]

$$Z_s = \frac{M_s(h_1, \{(x, y) \in \mathcal{D}_1 \mid s(h_1, x, y) = 1\})}{|\{(x, y) \in \mathcal{D}_1 \mid s(h_1, x, y) = 1\}|},\quad Z_g = \sum_s |\{(x, y) \in \mathcal{D}_1 \mid s(h_1, x, y) = 1\}| \tag{7}$$

In a case where an average value weighted based on the performance index and the evaluation of the pre-update model is used as a degradation index, a normalization coefficient is as follows.

[Formula 8]

$$Z_s = \frac{1}{|\{(x, y) \in \mathcal{D}_1 \mid s(h_1, x, y) = 1\}|}, Z_g = \sum_s M_s(h_1, \{(x, y) \in \mathcal{D}_1 \mid s(h_1, x, y) = 1\})|\{(x, y) \in \mathcal{D}_1 \mid s(h_1, x, y) = 1\}| \tag{8}$$

(C) Average weighted according to user's desire

In a case where an average value weighted based on an importance level designated by the user for each group s is used as a degradation index, $1/Z_s$ is a weight proportional to the importance level of the group s designated by the user. $Z_g$ is a value adjusted so that the maximum value becomes 1.

The index calculation unit 130 may not perform normalization. In this case, both $Z_s$ and $Z_g$ are 1.

The index calculation unit 130 may use cross entropy, mean square error, mean absolute error, compatibility index (back trust compatibility (BTC)) of PTL 1, or the like, not limited to Formula 1 described above, as a degradation index.

Here, a case where the index calculation unit 130 calculates a degradation index using the compatibility index (back trust compatibility (BTC)) of PTL 1 will be described. The following Formula 9 represents a BTC, and the following Formula 10 represents a degradation index using the BTC.

[Formula 9]

$$BTC = \frac{\sum_{(x,y)\in\mathcal{D}} [\![ [h_1(x) = y \wedge h_2(x) = y] }{\sum_{(x,y)\in\mathcal{D}} [\![ [h_1(x) = y]} \tag{9}$$

[Formula 10]

$$\text{Index} = 1 - BTC(h_1, h_2) = \frac{1}{\sum_i [\![ [h_1(x_i) = y_i]} \times \sum_{s\in\{s_i \mid i=1,\ldots,|\mathcal{D}|, s_i(f,x,y)=[\![ [x=x_i \wedge y=y_i]\}} \max (0, \frac{Acc(h_1, \{(x, y) \in \mathcal{D} \mid s(h_1, x, y) = 1\}) - Acc(h_2, \{(x, y) \in \mathcal{D} \mid}{1} \tag{10}$$

Here, in Formula 9, $h_n$ (x)=y means that an output for an input x is y in a machine learning model $h_n$. In Formula 10, $D_1$ and $D_2$ are as follows.

[Formula 11]

$$\mathcal{D}_1 = \mathcal{D}_2 = \mathcal{D} = \{(x_i, y_i)\}_{i=1}^{N} \tag{11}$$

(Example of Display Screen)

The output unit 140 outputs a degradation index on a display device. A method by which the output unit 140 displays a degradation index on the display device is not particularly limited. For example, the output unit 140 may output a degradation index for each group. The output unit 140 may output a plurality of types of degradation indexes.

Alternatively, the output unit 140 may output information on a group having a deterioration index lower than a predetermined threshold in comparison with the overall performance. In this case, the display device acquiring information from the output unit 140 may display the information in a state where a display form of a group condition associated with the degradation index lower than the threshold is changed based on the information.

The output unit 140 may output other information associated with the degradation index. For example, the output unit 140 may output the post-update model and the degradation index of the updated model in association with each other. Alternatively, the output unit 140 may output the post-update model, the degradation index, and the performance for each group in association with each other. For example, the output unit 140 may output the post-update model, the degradation index, and the performance of the post-update model for all the data in association with each other. In this case, the display device may display the post-update model, the degradation index, and the performance for all the evaluation data in association with each other. Hereinafter, the performance of the machine learning model for all the evaluation data will be referred to as an "overall performance".

Figure 2:
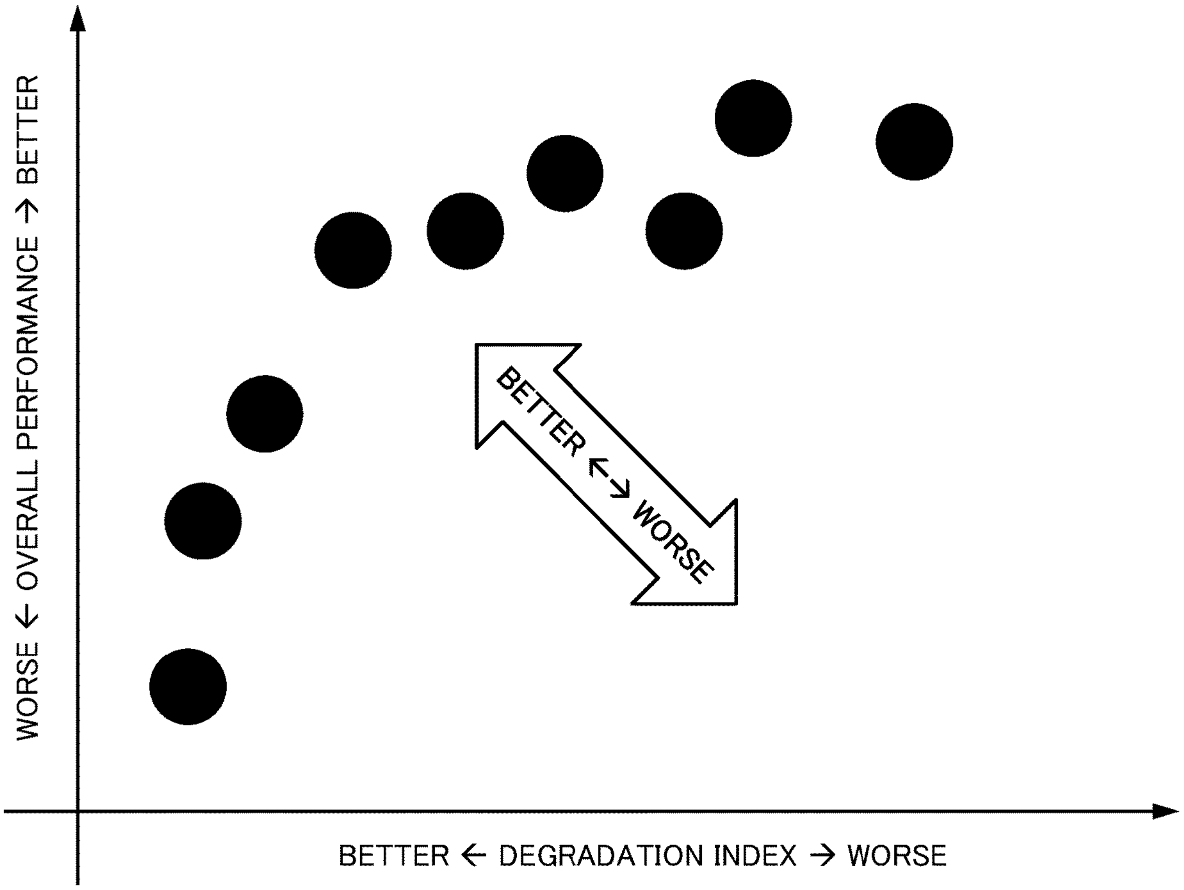
FIG. 2 is a diagram illustrating an example of a case where, in order to compare a plurality of post-update models, the post-update models are displayed in association with degradation indexes and overall performances.

FIG. 2 is a diagram illustrating an example of a case where, in order to compare a plurality of post-update models, the post-update models are displayed in association with degradation indexes and overall performances. In FIG. 2, a black circle indicates each of the post-update models. The coordinate position of the black circle indicates a degradation index and an overall performance of the post-update model. In FIG. 2, a model positioned further left indicates a post-update model having a better degradation index, and a model positioned higher indicates a post-update model having a better overall performance. That is, in FIG. 2, a post-update model positioned further left and higher indicates a post-update model that is better in both overall performance and degradation index.

The user may select a post-update model satisfying a desired overall performance and a desired degradation index from among the plurality of post-update models displayed as illustrated in FIG. 2. Alternatively, the output unit 140 may output a degradation index and a post-update model that satisfy a predetermined condition. For example, the output unit 140 may output a post-update model associated with a maximum or minimum degradation index in association with each other.

(Flow of Processing)

Figure 3:
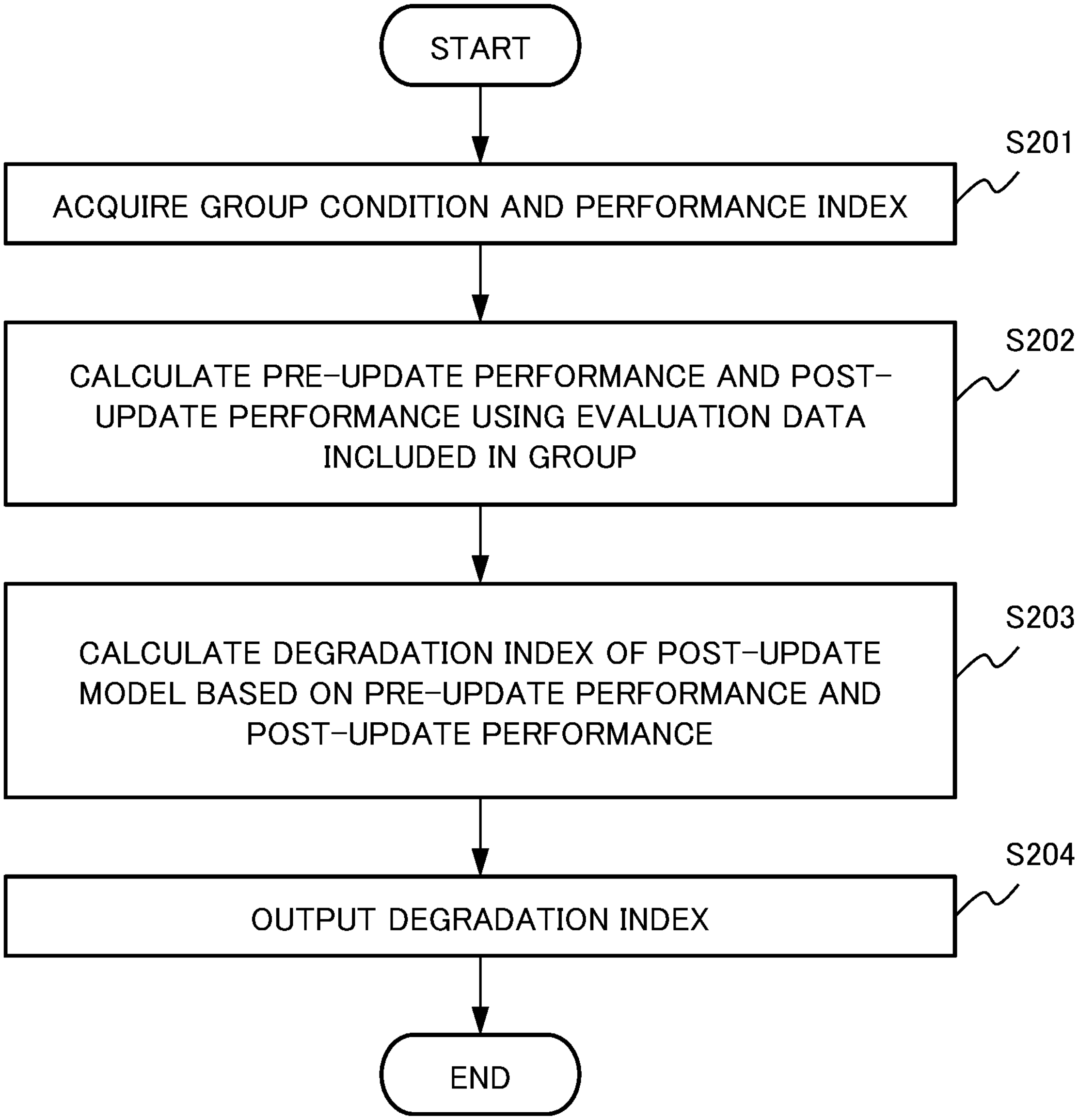
FIG. 3 is a flowchart illustrating an example of an operation of the information processing device.

FIG. 3 is a flowchart illustrating an example of an operation of the information processing device 10. The data acquisition unit 110 acquires a group condition (step S201). The group condition is a condition for specifying a group in which each piece of evaluation data is included. The performance calculation unit 120 calculates a pre-update performance and a post-update performance using the evaluation data included in the group (step S202). The pre-update performance is a performance evaluated according to the performance index using the evaluation data included in the group in relation to the pre-update model. The post-update performance is a performance evaluated according to the performance index using the evaluation data included in the group in relation to the post-update model. The index calculation unit 130 calculates a degradation index of the post-update model based on the pre-update performance and the post-update performance for each of the groups (step S203). The degradation index is an index indicating a deterioration in performance of the post-update model relative to the pre-update model. The output unit 140 outputs the degradation index (step S204).

(Example where Machine Learning Model is Evaluated Based on Degradation Index)

FIG. 4 is a diagram for explaining a degradation index of the information processing device 10. FIG. 4 illustrates prediction results of a pre-update model and three post-update models (machine learning model 1, machine learning model 2, and machine learning model 3) for 10 pieces of evaluation data.

A white circle in FIG. 4 indicates evaluation data of which a label matches a prediction result of each machine learning model. Further, in FIG. 4, the 10 pieces of evaluation data are divided into two groups (group 0 and group 1). The group 0 includes four pieces of evaluation data of evaluation data 1 to 4. The group 1 includes six pieces of evaluation data of evaluation data 5 to 10. In a case where the data is data regarding purchases of products, for example, the group 0 is data on weekdays, and the group 1 is data on weekends. FIG. 4 illustrates accuracies for all the evaluation data, the group 0, and the group 1 for each machine learning model. For example, the pre-update model is correct for 5 pieces of evaluation data (Nos. 1, 2, and 5-7) among the 10 pieces of evaluation data. Therefore, the accuracy of the pre-update model for all the evaluation data is 50%. The pre-update model is correct for two pieces of evaluation data (Nos. 1 and 2) among the four pieces of evaluation data of the group 0. Therefore, the accuracy of the pre-update model for the group 0 is 50%. The pre-update model is correct for three pieces of evaluation data (Nos. 5 to 7) among the six pieces of evaluation data of the group 1. Therefore, the accuracy of the pre-update model for the group 1 is 50%. The accuracies of the post-update models 1 to 3 are similarly obtained.

All of the accuracies of the machine learning models 1 to 3, which are post-update models, for all the evaluation data are 60%, which is improved over the accuracy of the pre-update model. Furthermore, the accuracies of the machine learning models 1 and 2 for the group 1 are 83%, which is improved over the accuracy of the pre-update model. In particular, the machine learning model 2 has a BTC of 80%, which is highest. Therefore, in terms of BTC, the machine learning model 2 is the best machine learning model. However, the accuracies of the machine learning models 1 and 2 for the group 0 are 25%, which deteriorates as compared with the accuracy of the pre-update model. On the other hand, the accuracy of the machine learning model 3 is improved for both the groups 0 and 1. Therefore, in a case where the groups are considered, the machine learning model 3 is the most desirable model. In addition, the degradation index calculated by the information processing device 10 is 0%, which is the lowest value, in the machine learning model 3. Therefore, the user of the information processing device 10 can select the machine learning model 3 of which the accuracy does not decrease in any group based on the degradation index.

As described above, the information processing device 10 includes a data acquisition unit 110, a performance calculation unit 120, an index calculation unit 130, and an output unit 140. The data acquisition unit 110 acquires a group condition for specifying a group in which each piece of evaluation data is included and a performance index for evaluating performances of models. The performance calculation unit 120 calculates a pre-update performance evaluated according to the performance index using evaluation data included in the group in relation to a pre-update model and a post-update performance evaluated according to the performance index using evaluation data included in the group in relation to a post-update model. The index calculation unit 130 calculates a degradation index indicating a deterioration in performance of the post-update model relative to the pre-update model based on the pre-update performance and the post-update performance for each of the groups. The output unit 140 outputs the degradation index.

As described above, the degradation index is an index in which the group is considered. That is, the information processing device 10 provides a model evaluation method in which a plurality of groups are considered. As a result, the user can evaluate a model in consideration of a plurality of groups. For example, the user can select a post-update model with reference to the graph as illustrated in FIG. 2. Furthermore, the information processing device 10 calculates a degradation index based on the post-update performance of the post-update model that has deteriorated as compared with the pre-update performance of the pre-update model as in Formula 1 or the like. Therefore, a performance of a post-update model having a degradation index of 0, like the model 3 in FIG. 4, does not decrease in any group. Therefore, the user can select a post-update model of which the performance does not decrease in any group by using a degradation index output by the information processing device 10.

Second Example Embodiment (Configuration of Device)

Figure 5:
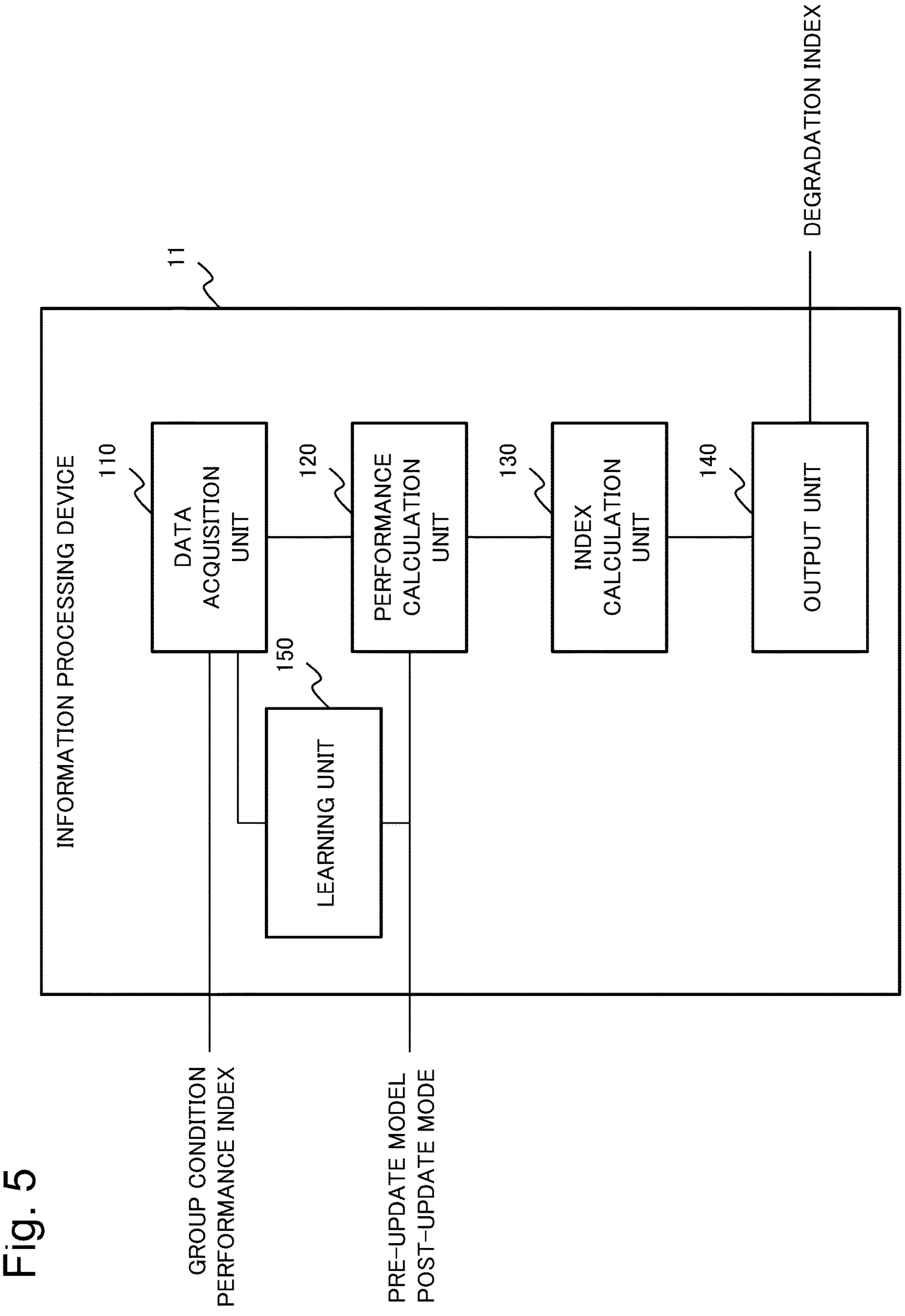
FIG. 5 is a block diagram illustrating an example of a configuration of an information processing device according to a second example embodiment.

FIG. 5 is a block diagram illustrating an example of a configuration of an information processing device 11 according to a second example embodiment. The information processing device 11 includes a learning unit 150 in addition to the configurations of the information processing device 10. Since the configurations other than the learning unit 150 are similar to those in the first example embodiment, the detailed description thereof will be omitted.

(Relearning Method 1: Method Using Weight for Evaluation Data)

The learning unit 150 executes relearning using the pre-update model and training data for relearning to create a post-update model. The training data used for relearning may be the same data as the evaluation data or may be other data. When performing relearning, the learning unit 150 uses a weight determined based on the pre-update performance for each group.

Specifically, the learning unit 150 uses a weight for a post-update performance for a group extracted based on one or more specific conditions designated in advance. For example, the learning unit 150 uses a weight $w_i$ of the following Formula 12. i is a subscript indicating an index of training data. That is, $w_i$ is a weight for i-th training data.

[Formula 12]

$$w_i = 1 + \lambda \times \sum_{s \in \{s \in \mathcal{S} \mid s(h_1, x_i, y_i) = 1\}} (M_s(h_1, \{(x, y) \in \mathcal{D}_1 \mid s(h_1, x, y) = 1\}))^{\tau} \quad (12)$$

λ and τ are hyperparameters that take values greater than 0, and are values that are adjusted depending on the object of the model. λ is a coefficient with respect to the sum of pre-update performances for each group. As λ increases, the weight of the evaluation data belonging to the group pointed out by the user increases. τ is a value adjusted according to a learning result. $D_1$ represents a set of evaluation data.

The learning unit 150 may store the created post-update model in a device that is not illustrated or may output the created post-update model to the performance calculation unit 120. The performance calculation unit 120 may acquire the post-update model from the learning unit 150, or may acquire the post-update model from a device that is not illustrated, similarly to the first example embodiment.

Figure 6:
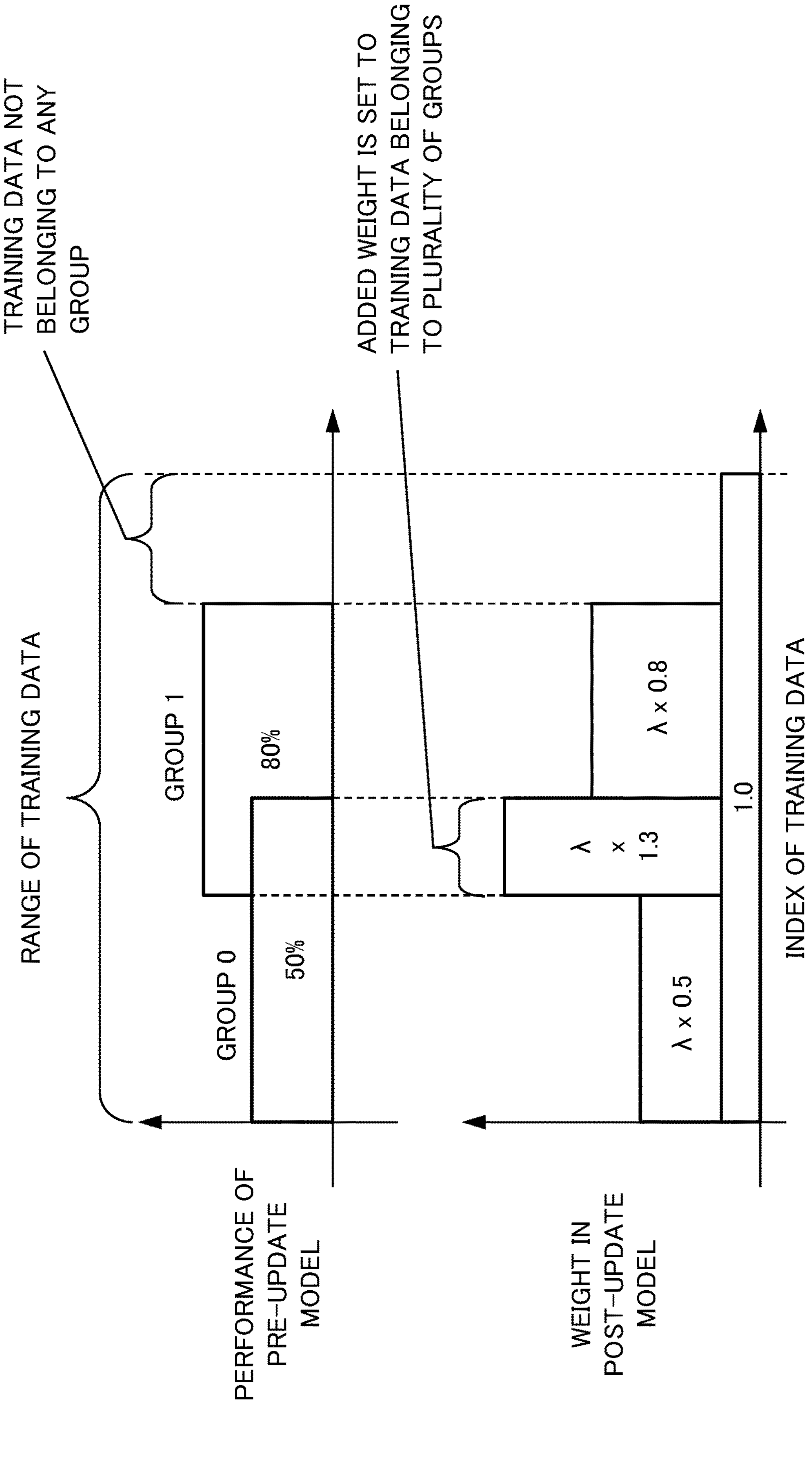
FIG. 6 is a diagram illustrating an example of weight setting.

FIG. 6 is a diagram illustrating an example of weight setting particularly in a case where evaluation data is used as training data for relearning. In FIG. 6, the upper graph shows a pre-update performance in each group. Specifically, in the pre-update model, the group 0 has showed a performance of 50%, and the group 1 has showed a performance of 80%. However, some data is overlapped between the groups 0 and 1. It is preferable that a group with a higher pre-update performance also exhibits a higher performance in the post-update model. Therefore, the learning unit 150 uses weights as shown in the lower graph.

A method in which the learning unit 150 sets weights will be described. First, the learning unit 150 gives a weight "1.0" to all the training data. Then, the learning unit 150 adds a weight proportional to the pre-update performance. Specifically, the learning unit 150 adds a weight proportional to the performance (0.5) to training data included in the group 0, and adds a weight proportional to the performance (0.8) to the training data belonging to the group 1. Then, the learning unit 150 adds a weight proportional to the value (1.3) obtained by adding the performance to training data belonging to both the groups 0 and 1. The learning unit 150 does not add a weight to data not belonging to any group.

Not limited to the weight setting in FIG. 6, for example, the learning unit 150 may add a weight proportional to the performance for the group with the highest performance to training data belonging to a plurality of groups. In this case, the weight is obtained, for example, by replacing Σ of Formula 12 with the max function. Alternatively, the learning unit 150 may use an upper limit value of a weight determined in advance. In a case where the weight exceeds the upper limit value, the learning unit 150 may use the upper limit value as the weight of the training data.

(Relearning Method 2: Method Using Loss Function to which Degradation Index is Introduced)

The learning unit 150 may directly create a post-update model using the degradation index of the post-update model, not limited to the performances for the groups. For example, the learning unit 150 may create a post-update model in such a way as to optimize the loss function using Formula 13.

[Formula 13]

$$L(h_2, \mathcal{D}_2) + \lambda\frac{1}{Z_g}\sum_{s\in S}[\![ [M_s(h_1, \{(x, y)\in\mathcal{D}_1 \mid s(h_1, x, y) = 1\}) \geq M_s(h_2, \{(x, y)\in\mathcal{D}_2 \mid s(h_2, x, y) = 1\})]\!]L'_s(h_2, \{(x, y)\in\mathcal{D}_2 \mid s(h_2, x, y) = 1\}) \quad (13)$$

$D_2$ represents training data for relearning. L is a normal loss function (including a regularization term and the like).

$$L'_s$$

is a loss function related to a group satisfying the condition s, and is a function whose gradient can be calculated. Examples of $$L'_s$$

are shown below using Formula 14 and Formula 15. When cross entropy is used, $$L'_s$$

is formula 14.

[Formula 14]

$$L'_s(h_2, \mathcal{D}) = -\frac{1}{|s|}\sum_{(x,y)\in\mathcal{D}}\ln h_2(y \mid x) \quad (14)$$

In a case where the sigmoid function is used, $$L'_s$$

is Formula 15.

[Formula 15]

$$L'_s(h_2, \mathcal{D}) = 1 - \frac{1}{|s|}\sum_{(x,y)\in\mathcal{D}}\sigma(\alpha h_2(y \mid x)) \quad (15)$$

Here, α is a hyperparameter indicating a weight of the function $h_2(y|x)$. $h_2(y|x)$ is a function that outputs a probability that is an output y for an input x of the machine learning model $h_2$.

The learning unit 150 may update the parameter of the machine learning model based on at least one of the performances for the group and the degradation index, not limited to the weight.

In this manner, the learning unit 150 of the information processing device 11 creates a post-update model by executing relearning based on at least one of the performances of the pre-update model for the group and the degradation index of the post-update model. Therefore, the information processing device 11 can create a post-update model that has executed appropriate relearning.

Example of Application

Here, an application example in a case where the present example embodiment is applied to the healthcare field will be described.

The information processing device 11 uses a machine learning model for performing healthcare for the user. In this case, the machine learning model is, for example, a model that predicts a health condition of the user based on biological data of the user acquired from a terminal device worn by the user.

The biological data of the user is, for example, data that is a blood oxygen concentration, a heart rate, a perspiration amount, a blood pressure, or other data affecting health condition of the user. The health condition of the user is, for example, an arrhythmia detection result, an atrial fibrillation detection result, a score indicating the quality of sleep, a score indicating the amount of exercise, or another index used to determine whether the user is healthy.

The information processing device 11 may create an action to be performed by the user or an action plan based on the prediction of the machine learning model. For example, the information processing device 11 collects biological data of the user from a wristwatch-type terminal device worn by the user. Then, the information processing device 11 displays a prediction value for the biological data on the terminal device of the user using the machine learning model. The information processing device 11 may calculate an action to be performed by the user or an action plan by applying a predetermined mathematical optimization calculation method to the prediction value, and display the action or the action plan on the terminal device.

The content output by the information processing device 11 is, for example, as follows, but is not limited thereto.

Scene 1 in Example of Application

When the user wakes up in the morning, the information processing device 11 outputs a morning exercise to be performed by the user based on data acquired from the terminal device. Before breakfast, the information processing device 11 outputs a breakfast menu having an appropriate nutritional balance based on data acquired from the terminal device.

Scene 2 in Example of Application

After work or school, the information processing device 11 outputs an appropriate exercise based on data acquired from the terminal device. Before lunch, the information processing device 11 outputs a lunch menu having an appropriate nutritional balance based on data acquired from the terminal device.

Scene 3 in Example of Application

In the evening, the information processing device 11 outputs an appropriate exercise based on data acquired from the terminal device. Before dinner, the information processing device 11 outputs a dinner menu having an appropriate nutritional balance based on data acquired from the terminal device.

Scene 4 in Example of Application

Before sleep, the information processing device 11 outputs an appropriate before-sleep stretching or breathing method based on data acquired from the terminal device.

In each use scene, the information processing device 11 may acquire an evaluation result as to whether the prediction result or the optimized proposal is appropriate from the user. The information processing device 11 calculates a degradation index of the machine learning model using the evaluation result of the user as evaluation data. Then, the information processing device 11 updates the machine learning model based on the deterioration index. In this manner, the information processing device 11 can update the machine learning model at all times by using the health data of the user and the evaluation result.

Third Example Embodiment

Figure 8:
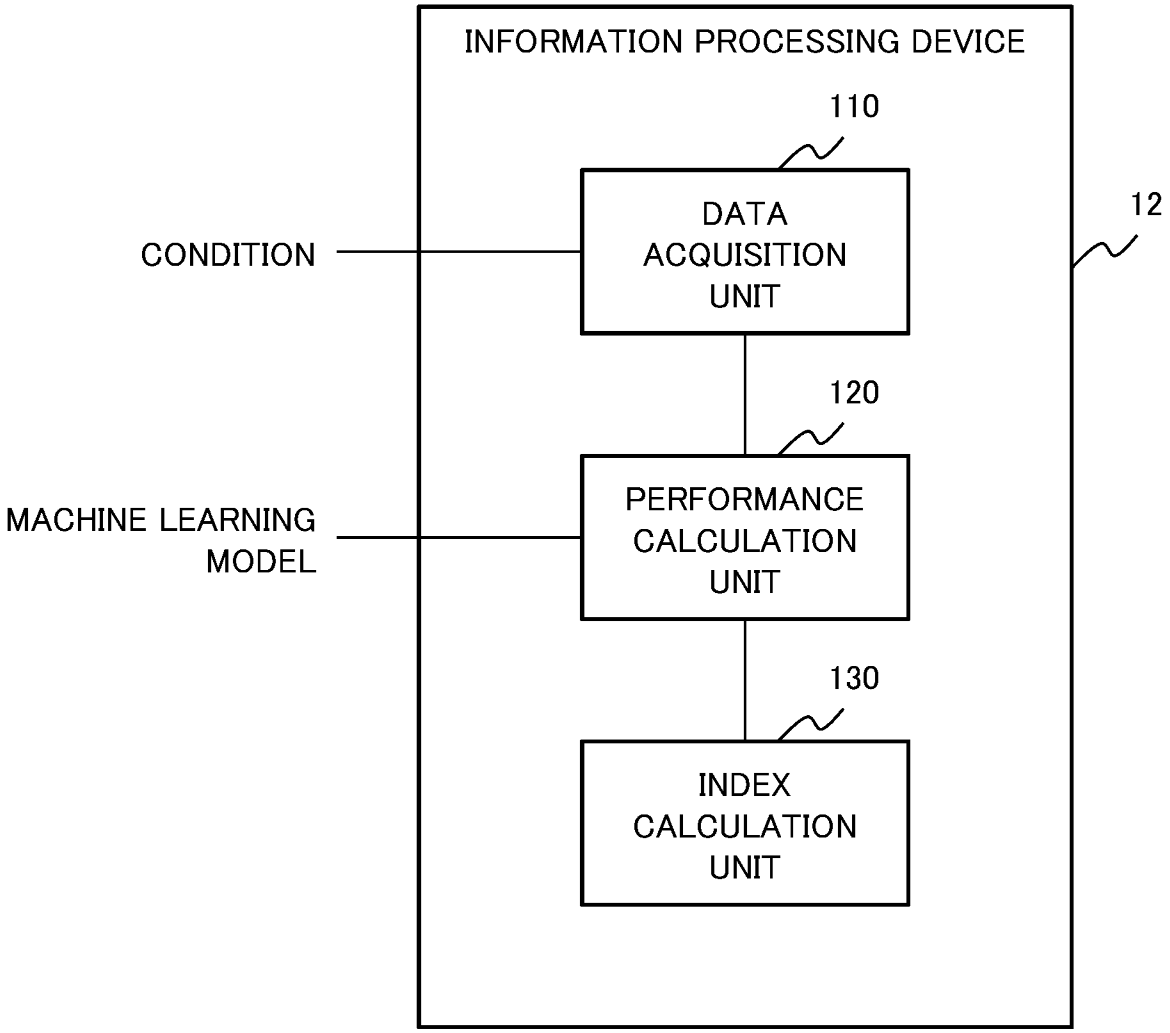
FIG. 8 is a block diagram illustrating an example of a configuration of an information processing device according to a third example embodiment.

The data of the plurality of groups are data sets specified for the respective conditions. Therefore, the information processing device 10 may be configured as in a third example embodiment to be described below. FIG. 8 is a block diagram illustrating an example of a configuration of an information processing device 12 according to the third example embodiment. The information processing device 12 includes a data acquisition unit 110, a performance calculation unit 120, and an index calculation unit 130. The data acquisition unit 110 acquires at least one condition for evaluation data of a machine learning model. The performance calculation unit 120 calculates a performance index of the machine learning model and a performance index of the machine learning model after being updated using a data set specified for each condition. The index calculation unit 130 calculates a deterioration index of a performance of the machine learning model based on the performance indexes before and after the machine learning model is updated. Using such a configuration, the information processing device 12 provides a model evaluation method in which a data set specified for each condition is considered.

The index calculation unit 130 calculates a deterioration index based on a difference between the performance index of the machine learning model and the performance index of the machine learning model after being updated. Furthermore, the information processing device 12 may include an output unit 140. In this case, the output unit 140 may output the deterioration index and an overall performance of the machine learning model after being updated. Furthermore, the output unit 140 may output the machine learning model, the machine learning model after being updated, data for which the machine learning model is correct, data for which the machine learning model after being updated is correct, a performance for each condition, and an overall performance of the machine learning model after being updated.

Fourth Example Embodiment

Figure 9:
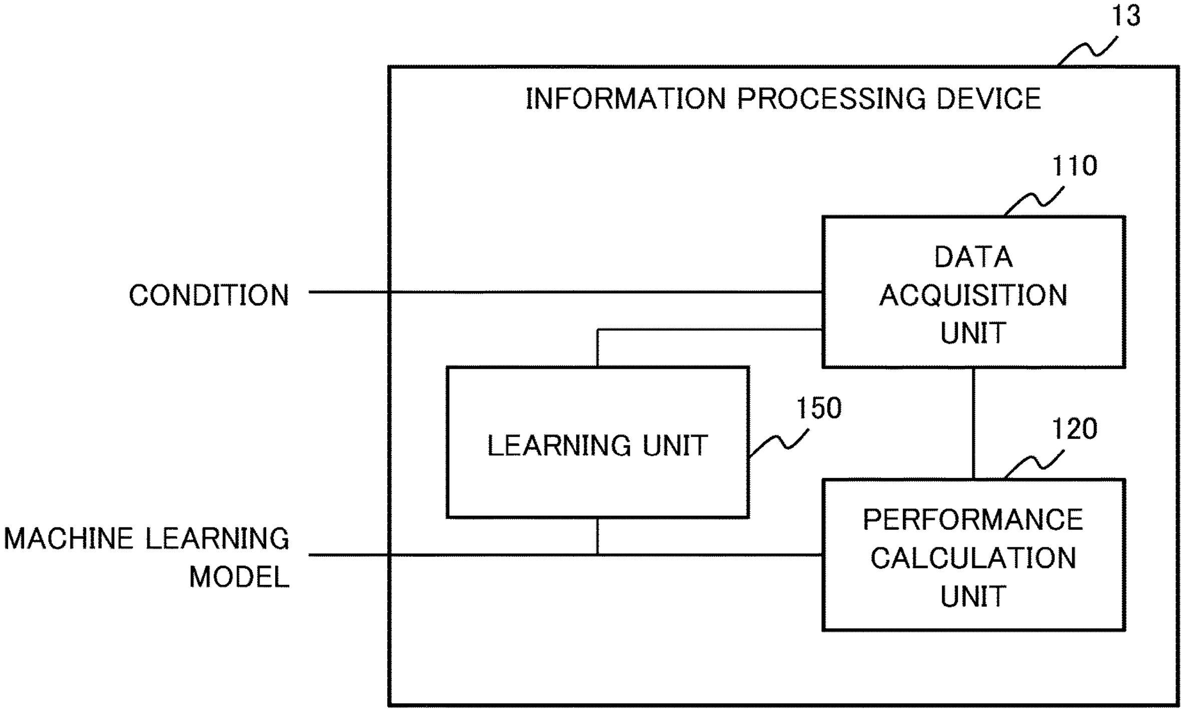
FIG. 9 is a block diagram illustrating an example of a configuration of an information processing device according to a fourth example embodiment.

The information processing device 11 may be configured as in a fourth example embodiment to be described below. FIG. 9 is a block diagram illustrating an example of a configuration of an information processing device 13 according to the fourth example embodiment. The information processing device 13 includes a data acquisition unit 110, a performance calculation unit 120, and a learning unit 150. The data acquisition unit 110 acquires at least one condition for evaluation data of a machine learning model. The performance calculation unit 120 calculates a performance index of the machine learning model using a data set specified for each condition. The learning unit 150 causes the machine learning model to perform relearning based on the performance index. The learning unit 150 causes the machine learning model to perform relearning by using a weight set based on the performance index of the machine learning model for the data set.

The information processing device 13 may include an index calculation unit 130. In this case, the performance calculation unit 120 further calculates a performance index of the machine learning model after being updated. Then, the index calculation unit 130 calculates a deterioration index of a performance of the machine learning model based on the performance indexes before and after the machine learning model is updated. Then, the learning unit 150 causes the machine learning model to perform relearning using a loss function related to the deterioration index of the machine learning model after being updated.

Hardware Configuration

Next, a hardware configuration of each of the information processing devices 10 to 13 will be described. Each component of each of the information processing devices 10 to 13 may be configured by a hardware circuit. Alternatively, each component of each of the information processing devices 10 to 13 may be configured using a plurality of devices connected to each other via a network. For example, each of the information processing devices 10 to 13 may be configured using cloud computing. Alternatively, a plurality of components of each of the information processing devices 10 to 13 may be configured by one piece of hardware. Alternatively, each of the information processing devices 10 to 13 may be implemented as a computer device including a processor, a read-only memory (ROM), a random access memory (RAM), and a network interface card. As the processor, for example, a central processing unit (CPU), a graphic processing unit (GPU), a digital signal processor (DSP), a micro processing unit (MPU), a floating point number processing unit (FPU), a physics processing unit (PPU), a tensor processing unit (TPU), a quantum processor, a microcontroller, or a combination thereof can be used.

Figure 7:
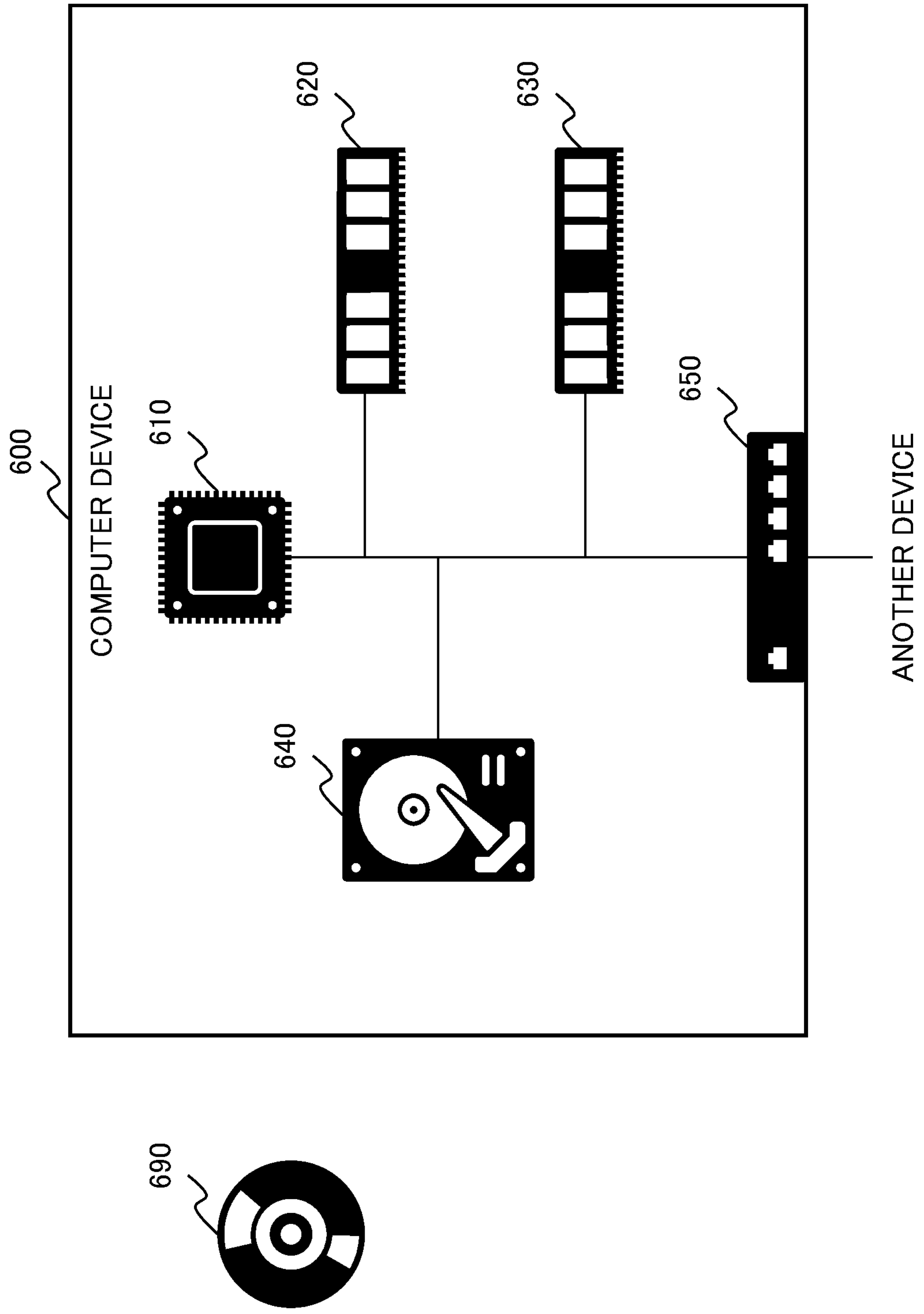
FIG. 7 is a block diagram illustrating an example of a hardware configuration.

FIG. 7 is a block diagram illustrating a configuration of a computer device 600 which is an example of a hardware configuration of each of the information processing devices 10 to 13. The computer device 600 includes a processor 610, a ROM 620, a RAM 630, a storage device 640, and a network interface 650.

The processor 610 reads a program from at least one of the ROM 620 and the storage device 640. Then, the processor 610 controls the RAM 630, the storage device 640, and the network interface 650 based on the read program. Then, the computer device 600 including the processor 610 controls these components to implement functions as the data acquisition unit 110, the performance calculation unit 120, the index calculation unit 130, the output unit 140, and the learning unit 150. As described above, the computer device 600 may implement functions as a combination of hardware and software. The processor 610 may read a program included in a recording medium 690, which stores the program in a computer readable manner, using a recording medium reading device that is not illustrated. Alternatively, the processor 610 may receive a program from an external device that is not illustrated via the network interface 650, store the program in the RAM 630 or the storage device 640, and operate based on the stored program.

The ROM 620 stores programs to be executed by the processor 610 and fixed data. The ROM 620 is, for example, a programmable ROM (P-ROM) or a flash ROM. The RAM 630 temporarily stores programs to be executed by the processor 610 and data. The RAM 630 is, for example, a dynamic RAM (D-RAM). The storage device 640 stores data and programs to be stored by the computer device 600 for a long period of time. The storage device 640 may operate as a temporary storage device of the processor 610. The storage device 640 is, for example, a hard disk device, a solid state drive (SSD), or a disk array device.

The ROM 620 and the storage device 640 are non-volatile (non-transitory) recording media. On the other hand, the RAM 630 is a volatile (transitory) recording medium. The processor 610 can operate based on programs stored in the ROM 620, the storage device 640, and the RAM 630. That is, the processor 610 can operate using either a non-volatile recording medium or a volatile recording medium. When implementing each function, the processor 610 may use at least one of the RAM 630 and the storage device 640 as a medium for temporarily storing a program and data.

The network interface 650 relays exchange of data with an external device that is not illustrated via a network. The network interface 650 is, for example, a local area network (LAN) card. Furthermore, the network interface 650 may be used in a wireless manner, not limited to the wired manner.

The computer device 600 configured as described above implements the functions of the information processing devices 10 to 13 by executing the operations of the components of the information processing devices 10 to 13.

Some or all of the above-described example embodiments may be described as in the following supplementary notes, but are not limited to the following supplementary notes.

Supplementary Note 1

An information processing device including:

a data acquisition means configured to acquire at least one condition for evaluation data of a machine learning model;

a performance calculation means configured to calculate a performance index of the machine learning model and a performance index of the machine learning model after being updated using a data set specified for each of the at least one condition; and an index calculation means configured to calculate a deterioration index of a performance of the machine learning model based on the performance indexes before and after the machine learning model is updated.

Supplementary Note 2

The information processing device according to supplementary note 1, in which the index calculation means calculates the deterioration index based on a difference between the performance index of the machine learning model and the performance index of the machine learning model after being updated.

Supplementary Note 3

The information processing device according to supplementary note 1 or 2, further including:

an output means configured to output the machine learning model after being updated, the deterioration index, and an overall performance of the machine learning model after being updated.

Supplementary Note 4

The information processing device according to supplementary note 3, in which the output means outputs the machine learning model, the machine learning model after being updated, data for which the machine learning model is correct, data for which the machine learning model after being updated is correct, a performance for each of the at least one condition, and the overall performance of the machine learning model after being updated.

Supplementary Note 5

An information processing device including:

a data acquisition means configured to acquire at least one condition for evaluation data of a machine learning model;

a performance calculation means configured to calculate a performance index of the machine learning model using a data set specified for each of the at least one condition; and a learning means configured to cause the machine learning model to perform relearning based on the performance index.

Supplementary Note 6

The information processing device according to supplementary note 5, in which the learning means causes the machine learning model to perform relearning by using a weight set based on the performance index of the machine learning model for the data set.

(Supplementary Note 7)

The information processing device according to supplementary note 5 or 6, in which the performance calculation means further calculates a performance index of the machine learning model after being updated, the information processing device further includes an index calculation means configured to calculate a deterioration index of a performance of the machine learning model based on the performance indexes before and after the machine learning model is updated, and the learning means causes the machine learning model to perform relearning using a loss function related to the deterioration index of the machine learning model after being updated.

Supplementary Note 8

The information processing device according to any one of supplementary notes 1 to 7, in which the machine learning model is a model that predicts a health condition of a user with respect to health data of the user acquired from a terminal of the user.

Supplementary Note 9

The information processing device according to any one of supplementary notes 1, 2, 3, and 7, in which the machine learning model is a model that predicts a health condition of a user with respect to health data of the user acquired from a terminal of the user, the data acquisition means acquires an evaluation result of the user for a prediction result as evaluation data of the machine learning model, and the index calculation means calculates the deterioration index by using the evaluation result of the user for the prediction result.

Supplementary Note 10

An information processing method including:

acquiring at least one condition for evaluation data of a machine learning model;

calculating a performance index of the machine learning model and a performance index of the machine learning model after being updated using a data set specified for each of the at least one condition; and calculating a deterioration index of a performance of the machine learning model based on the performance indexes before and after the machine learning model is updated.

Supplementary Note 11

A recording medium recording a program for causing a computer to execute:

acquiring at least one condition for evaluation data of a machine learning model;

calculating a performance index of the machine learning model and a performance index of the machine learning model after being updated using a data set specified for each of the at least one condition; and calculating a deterioration index of a performance of the machine learning model based on the performance indexes before and after the machine learning model is updated.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

REFERENCE SIGNS LIST

10 Information processing device
11 Information processing device
12 Information processing device
13 Information processing device
110 Data acquisition unit
120 Performance calculation unit
130 Index calculation unit
140 Output unit
150 Learning unit
600 Computer device
610 Processor
620 ROM
630 RAM
640 Storage device
650 Network interface
690 Recording medium

What is claimed is:

1. An information processing device comprising: a memory; and at least one processor coupled to the memory, the processor performing operations, the operations comprising:

acquiring at least one condition for evaluation data of a machine learning model;

calculating a performance index of the machine learning model and a performance index of the machine learning model after being updated using a data set specified for each of the at least one condition; and calculating a deterioration index of a performance of the machine learning model based on the performance indexes before and after the machine learning model is updated;

determining, based on the deterioration index, whether the performance of the machine learning model after being updated has deteriorated for at least one specific condition of the at least one condition;

in a case where the deterioration index indicates that the performance has deteriorated for the at least one specific condition, causing the machine learning model to perform relearning by adjusting parameters of the machine learning model based on the performance indexes for the at least one specific condition; and in a case where the deterioration index does not exceed a predetermined threshold, outputting the machine learning model after being updated.

2. The information processing device according to claim 1, wherein the operations further comprise: calculating the deterioration index based on a difference between the performance index of the machine learning model and the performance index of the machine learning model after being updated.

3. The information processing device according to claim 1, wherein the operations further comprise:

outputting the machine learning model after being updated, the deterioration index, and an overall performance of the machine learning model after being updated.

4. The information processing device according to claim 3, wherein the operations further comprise: outputting the machine learning model, the machine learning model after being updated, data for which the machine learning model is correct, data for which the machine learning model after being updated is correct, a performance for each of the at least one condition, and the overall performance of the machine learning model after being updated.

5. The information processing device according to claim 1, wherein the operations further comprise: causing the machine learning model to perform relearning based on the performance index.

6. The information processing device according to claim 5, wherein the operations further comprise: causing the machine learning model to perform relearning by using a weight set based on the performance index of the machine learning model for the data set.

7. The information processing device according to claim 5, wherein the operations further comprise: calculating a performance index of the machine learning model after being updated, calculating a deterioration index of a performance of the machine learning model based on the performance indexes before and after the machine learning model is updated, and causing the machine learning model to perform relearning optimizing a loss function related to the deterioration index of the machine learning model after being updated.

8. The information processing device according to claim 1 wherein the machine learning model is a model that predicts a health condition of a user with respect to health data of the user acquired from a terminal of the user.

9. The information processing device according to claim 1, wherein The machine learning model is a model that predicts a health condition of a user with respect to health data of the user acquired from a terminal of the user, and the operations further comprise:

acquiring an evaluation result of the user for a prediction result as evaluation data of the machine learning model, and calculating the deterioration index by using the evaluation result of the user for the prediction result.

10. An information processing method comprising:

acquiring at least one condition for evaluation data of a machine learning model;

calculating a performance index of the machine learning model and a performance index of the machine learning model after being updated using a data set specified for each of the at least one condition; and calculating a deterioration index of a performance of the machine learning model based on the performance indexes before and after the machine learning model is updated;

determining, based on the deterioration index, whether the performance of the machine learning model after being updated has deteriorated for at least one specific condition of the at least one condition;

in a case where the deterioration index indicates that the performance has deteriorated for the at least one specific condition, causing the machine learning model to perform relearning by adjusting parameters of the machine learning model based on the performance indexes for the at least one specific condition; and in a case where the deterioration index does not exceed a predetermined threshold, outputting the machine learning model after being updated.

11. A non-transitory computer-readable recording medium recording a program for causing a computer to execute:

acquiring at least one condition for evaluation data of a machine learning model;

calculating a performance index of the machine learning model and a performance index of the machine learning model after being updated using a data set specified for each of the at least one condition; and calculating a deterioration index of a performance of the machine learning model based on the performance indexes before and after the machine learning model is updated;

determining, based on the deterioration index, whether the performance of the machine learning model after being updated has deteriorated for at least one specific condition of the at least one condition; in a case where the deterioration index indicates that the performance has deteriorated for the at least one specific condition, causing the machine learning model to perform relearning by adjusting parameters of the machine learning model based on the performance indexes for the at least one specific condition; and in a case where the deterioration index does not exceed a predetermined threshold, outputting the machine learning model after being updated.

* * * * *